United States Patent
Tang (10) Patent No.: US 8,561,469 B2
(45) Date of Patent: Oct. 22, 2013

(54) THREE-DIMENSIONAL MECHANICAL ULTRASONIC PROBE

(75) Inventor: Shengli Tang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 188 days.

(21) Appl. No.: 12/952,798

(22) Filed: Nov. 23, 2010

(65) Prior Publication Data

US 2011/0126627 A1 Jun. 2, 2011

(30) Foreign Application Priority Data

Dec. 2, 2009 (CN) .......................... 2009 1 0253894

(51) Int. Cl.
*G01N 29/26* (2006.01)

(52) U.S. Cl.
USPC ............................................................ 73/635

(58) Field of Classification Search
USPC ............ 73/635, 618–620; 600/407, 437, 459
See application file for complete search history.

(56) References Cited

U.S. PATENT DOCUMENTS

| | | | |
|---|---|---|---|
| 4,418,698 A | 12/1983 | Dory | |
| 4,688,576 A | 8/1987 | Meyers | |
| 4,785,816 A | 11/1988 | Dow et al. | |
| 4,807,634 A * | 2/1989 | Enjoji et al. | 600/437 |
| 6,569,100 B2 * | 5/2003 | Okawa et al. | 600/445 |
| 7,240,556 B2 * | 7/2007 | Georgeson et al. | 73/641 |
| 7,554,245 B2 * | 6/2009 | Hasegawa | 310/334 |
| 7,998,077 B2 * | 8/2011 | Kim | 600/459 |
| 2008/0161694 A1 * | 7/2008 | Kim | 600/459 |
| 2008/0161695 A1 | 7/2008 | Kim et al. | |
| 2011/0071399 A1 * | 3/2011 | Tang et al. | 600/459 |

FOREIGN PATENT DOCUMENTS

| | | |
|---|---|---|
| CN | 1720006 A | 1/2006 |
| CN | 1880921 A | 12/2006 |
| CN | 1011464831 A | 3/2008 |
| CN | 201247227 Y | 5/2009 |
| EP | 1 744 178 A2 | 1/2007 |

* cited by examiner

*Primary Examiner* — J M Saint Surin
(74) *Attorney, Agent, or Firm* — Stoel Rives, LLP; Kory D. Christensen (57) ABSTRACT

A three-dimensional mechanical ultrasound probe includes a base; a transducer for emitting an ultrasonic signal; a driven wheel with a hole, the driven wheel being connected to the transducer, the transducer being swung by the driven wheel; a motor fixed on the base; and a transmission system connected to the motor and a first rope, the transmission system being driven by the motor, the first rope being driven by the transmission system, wherein the first rope is connected to the transmission system and a rope adjusting dowel; and wherein the adjusting dowel is pivotably inserted into the hole of the driven wheel.

6 Claims, 7 Drawing Sheets

FIG. 8 ly referred to as a three-dimensional mechanical ultrasonic probe.

THREE-DIMENSIONAL MECHANICAL ULTRASONIC PROBE

CROSS-REFERENCE TO RELATED APPLICATIONS

This application claims the benefit of Chinese Patent Application No. 200910253894.4, filed on Dec. 2, 2009, which is incorporated herein by reference.

TECHNICAL FIELD

The present disclosure relates generally to diagnostic ultrasound systems, and more particularly to a transmission system of an ultrasonic probe.

SUMMARY OF THE INVENTION

A three-dimensional mechanical ultrasonic probe is disclosed in which the effective length and tension of ropes can be adjusted.

DETAILED DESCRIPTION

An ultrasonic probe providing three-dimensional imaging is generally referred to as a three-dimensional mechanical probe. The probe typically includes a step motor as drive power source and a transducer swinging between a certain angle range driven by a transmission system, the transmission system being driven by the step motor in response to a control signal.

Figure 1:
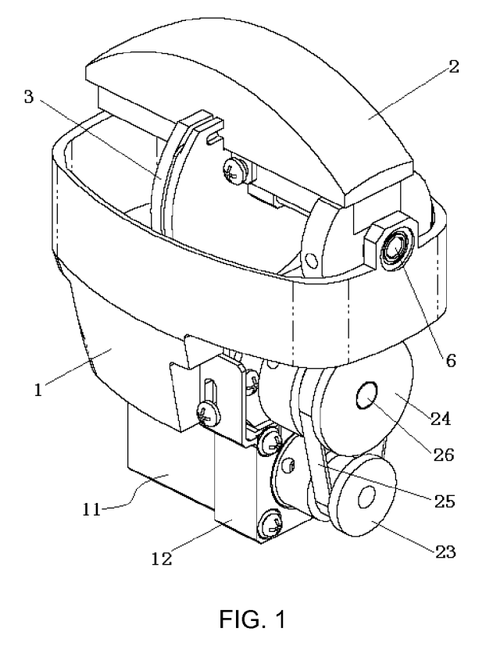
FIG. 1 is a schematic view of a three-dimensional mechanical probe.
Figure 2:
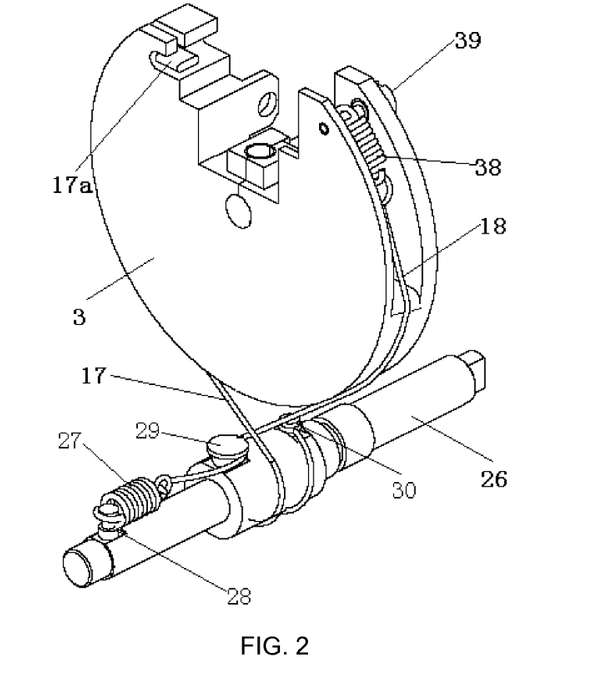
FIG. 2 is a schematic view of a method for connecting ropes within the probe.
Figure 3:
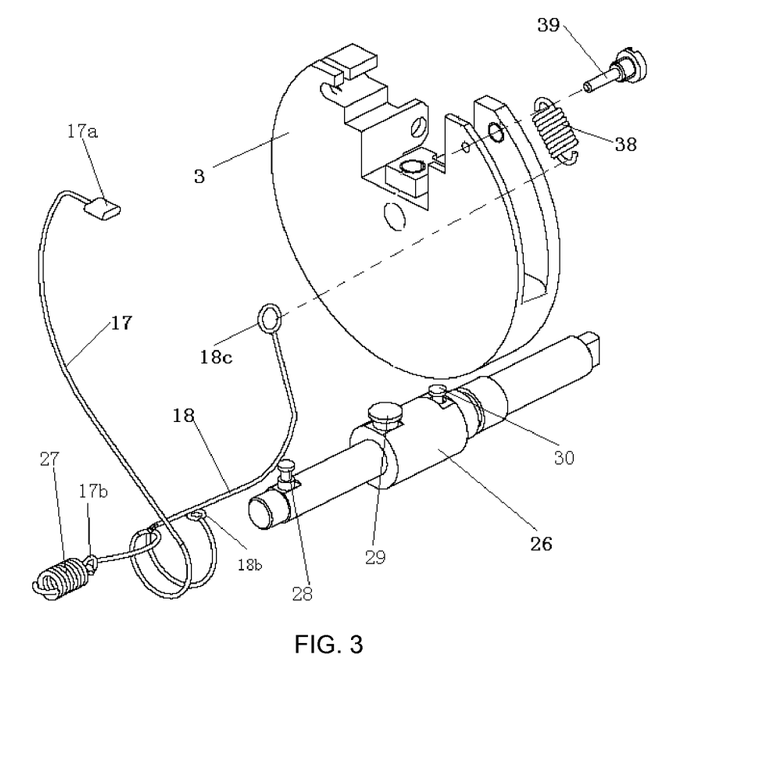
FIG. 3 is an exploded view of a method for connecting ropes within the probe.

The transmission system may be realized as follows. As shown in FIGS. 1-3, a motor 11 is fixed on a base 1 by a motor support 12. A driving timing pulley 23 is fixed on an output shaft of the motor 11. The output of the motion of the motor 11 is transferred from the driving timing pulley 23 to a driven timing pulley 24 by a timing belt 25. The driven timing pulley 24 is fixed on a driving shaft 26. The driving shaft 26 is pivotably mounted to the base 1. The driven wheel 3 is pivotably mounted to the base 1 by a transducer rotation shaft 6. The transducer 2 is fixed on the driven wheel 3. The driving shaft 26 drives the driven wheel 3 to rotate by a first rope 17 and a second rope 18, which are connected to the driven wheel 3. The transducer 2 is swung by the driven wheel 3. As illustrated, the transducer 2 is swung by the motor 11.

To ensure the precision of the swinging angle and avoid the ropes falling off, the first rope 17 and the second rope 18 must be tightened when the transducer 2 is rotating. One end hook of a first spring 27 hooks a joint pin 28, which is fixed on the driving shaft 26, and the other end hook of the first spring 27 hooks a buckle 17b of one end of the first rope 17. The first rope 17 rounds a turning pin 29, which is fixed on the driving shaft 26 and twists on the driving shaft 26, then twists on the driven wheel 3, a knot 17a being locked on the driven wheel 3.

One end hook of a second spring 38 hooks a joint pin 39, which is fixed on the driven wheel 3, and the other end hook of the second spring 38 hooks the buckle 18c of one end of the second rope 18. The second rope 18 twists on the driven wheel 3 and the driving shaft 26, the buckle 18b hooks a joint pin 30, which is fixed on the driving shaft 26. In order to keep the first rope 17 and the second rope 18 tightened, the first spring 27 and the second spring 38 should have certain tensile strain after they are assembled.

During the assembling process, the first spring 27 or the second spring 38 imposes a force to twist the first rope 17 and the second rope 18 on the driving shaft 26 and the driven wheel 3, and there is certain force on the first spring 27 and the second spring 38. If the ropes are shorter, the two springs impose more force, and the ropes are tighter. If the ropes are longer, the two springs impose less force, such that the ropes may not be tightened. Whether ropes are tight or loose, the ropes must be replaced to meet tension requirements. It is difficult to adjust the tension of the ropes and assemble the ropes.

To solve these problems, an ultrasonic probe is provided, in which the effective length of the ropes can be adjusted and it is easy to assemble the ropes and adjust the tension of the ropes.

According to one aspect of the disclosure, a three-dimensional mechanical ultrasonic probe includes a base, a transducer for emitting an ultrasonic signal, a driven wheel with a hole, the driven wheel being connected to the transducer, the transducer being swung by the driven wheel. A motor is fixed on the base, and a transmission system is connected to the motor and a first rope, the transmission system being driven by the motor. The first rope is driven by the transmission system. The first rope is connected to the transmission system and a rope adjusting dowel. The adjusting dowel is pivotably inserted into the hole of the driven wheel.

According to another aspect, the ultrasonic probe also includes a second rope, one end of the second rope connecting with the transmission system. The driven wheel includes a second spring, and the other end of the second rope connects with the second spring.

According to yet another aspect, a three-dimensional mechanical ultrasonic probe includes a base, a transducer, a driven wheel, a motor, a transmission system, a rope, and an adjusting dowel, the motor being fixed to the base. The motor drives the transmission system, and the transmission system drives the rope. One end of the rope connects with the driven wheel. The rope drives the driven wheel. The transducer is fixed on the driven wheel which has a hole, and the adjusting dowel is pivotably inserted into the driven wheel, and the other end of the rope being twisted on the adjusting dowel.

In still another aspect, the three-dimensional mechanical ultrasonic probe includes an adjusting dowel for adjusting the effective length of the ropes by rotating the adjusting dowel, so as to prevent the rope from becoming too loose or too tight.

Referring generally to FIGS. 1-8, a three-dimensional mechanical ultrasonic probe includes a base 1, a transducer 2, a driven wheel 3 with a hole, a motor 11, a transmission system, an adjusting dowel 41, and a first rope 17. In one embodiment, the motor 11 is fixed on the base 1 and drives the transmission system. The first rope 17 is connected to the transmission system and driven by the transmission system. The driven wheel 3 is driven by the first rope 17 and connects with the transducer 2, which swings with the driven wheel 3. The adjusting dowel 41 is pivotably inserted into the hole of the driven wheel 3. One end of the first rope 17 is twisted on the adjusting dowel 41. By rotating the adjusting dowel 41, the length of the rope twisted on the adjusting dowel 41 is adjusted, thus the effective length of the first rope 17 which drives the driven wheel 3 to rotate is adjusted. The effective length is the actual effective length for driving the driven wheel 3 to rotate, not including the length of the rope twisted on the adjusting dowel 41.

In one embodiment, the transmission system includes a driving timing pulley 23, a timing belt 25, a driven timing pulley 24 and a driving shaft 26. The motor 11 is fixed on the base 1 by the motor support 12. The driving timing pulley 23 is fixed on the output shaft of the motor 11. The output of the motion of the motor 11 is transferred from the driving timing pulley 23 to the driven timing pulley 24 by the timing belt 25. The driven timing pulley 24 is fixed on the driving shaft 26, the driving shaft 26 is pivotably mounted to the base 1.

In the illustrated embodiment, the driven wheel 3 is pivotably fixed on the base 1 by the transducer rotation shaft 6. The transducer 2 is fixed on the driven wheel 3. The driving shaft 26 drives the driven wheel 3 to rotate by the rope 17 which is connected to the driven wheel 3. The transducer 2 is driven to rotate by the driven wheel 3. A skilled artisan will recognize that other similar transmission systems can be applied for rotating the driven wheel 3 with the rope 17 by the motor 11.

Figure 4:
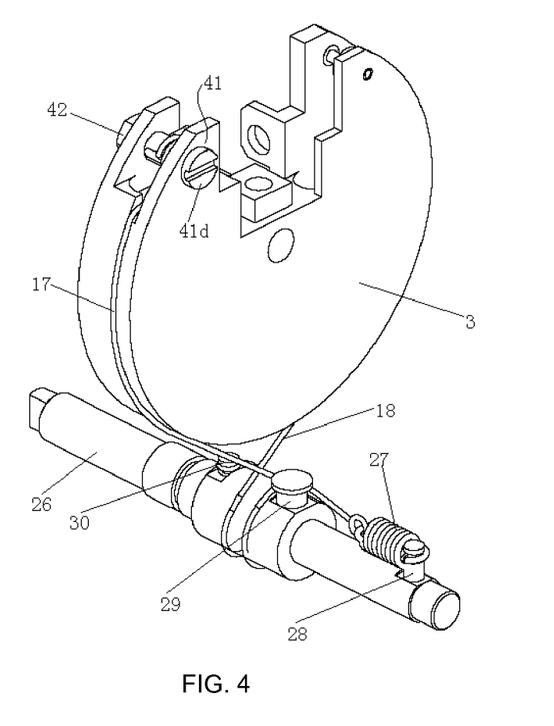
FIG. 4 is a schematic view of a method for connecting ropes within the probe.
Figure 5:
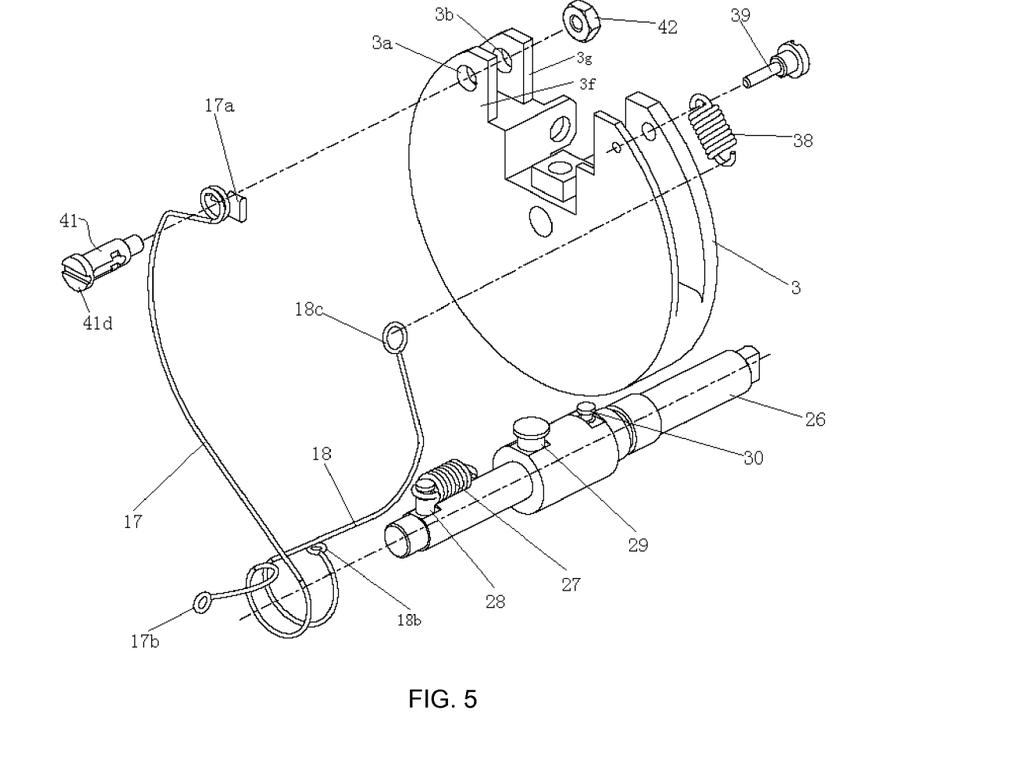
FIG. 5 is an exploded view of a method for connecting ropes within the probe.

In one embodiment, a second rope 18 is provided, as shown in FIG. 4 and FIG. 5. The buckle 18b on one end of the second rope 18 hooks the connecting pin 30, and the second rope 18 twists on the driving shaft 26 and the driven wheel 3. The buckle 18c on the other end of the second rope 18 hooks the hook of the second spring 38. The second spring 38 connects with the driven wheel 3 by the spring connecting pin 39 on the driven wheel 3. The hook on one end of the first spring 27 hooks the spring connecting pin 28 on the driving shaft 26, the hook on the other end of the first spring 27 hooks the buckle 17b on one end of the first rope 17.

In the depicted embodiment, the first rope 17 twists on the driving shaft 26 and the driven wheel 3 successively, and the buckle 17a on the other end of the first rope 17 is connected to the adjusted dowel 41. A reverse reset torsional spring fixed on the transducer rotating shaft 6 can be used for repeatedly swinging the driven wheel 3 with the first rope 17 instead of the second rope 18.

Figure 6:
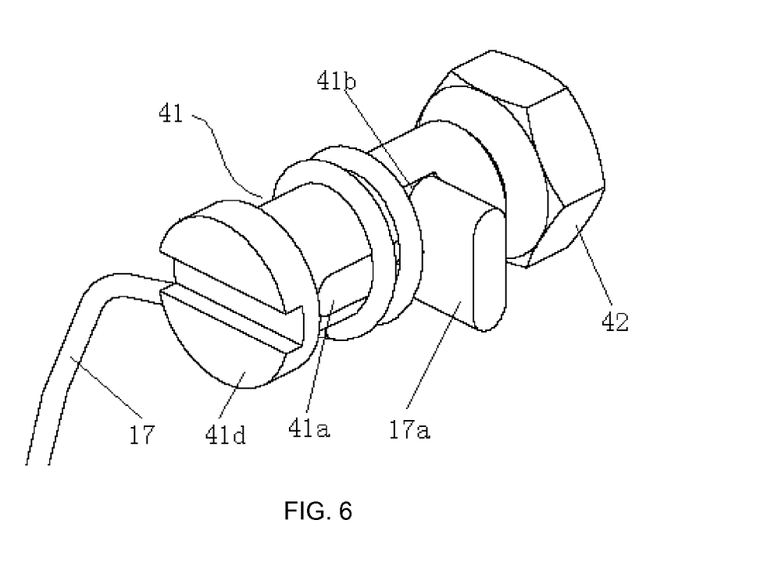
FIG. 6 is a schematic view of a structure for adjusting the tension of a rope.
Figure 7:
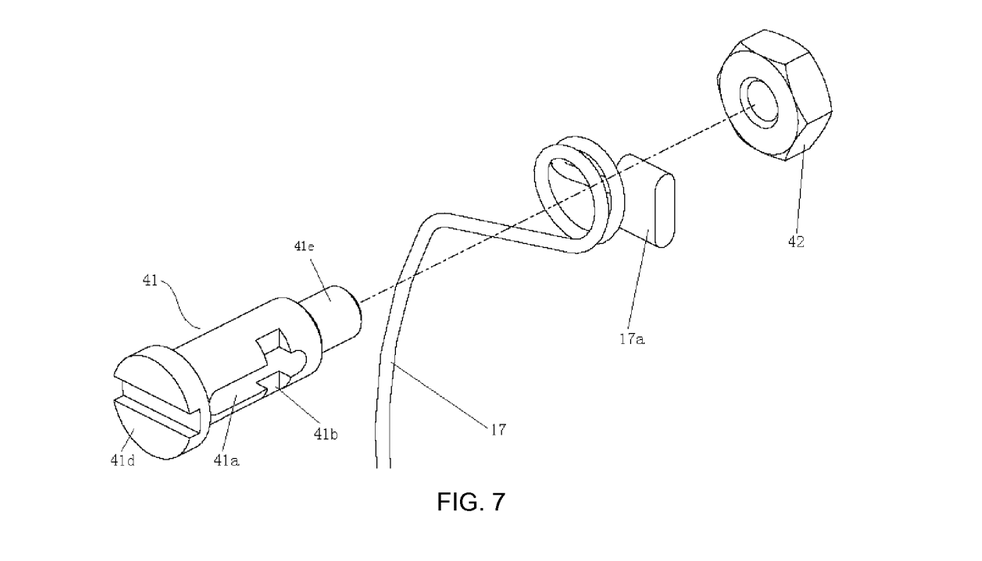
FIG. 7 is an exploded view of a method for connecting a rope and a dowel.

One embodiment of a method for connecting the first rope 17 and the adjusting dowel 41 is shown in FIG. 6 and FIG. 7. The adjusting dowel 41 may include a waist-shaped hole 41a and a slot 41b. The knot 17a may pass through the hole 41a. When assembling the first rope 17, the adjusting dowel 41 is inserted into the holes 3a and 3b on the driven wheel 3, and then the knot 17a of the first rope 17 passes through the waist-shaped hole, rotates 90 degrees and is blocked in the slot 41b. For convenient assembly, the knot 17a may be processed previously before being connected to the adjusting dowel 41.

In the case of the adjusting dowel 41 with a right-hand screw, the adjustment method may be performed as follows. Rotate the adjusting dowel 41 counter-clockwise and wind the first rope 17 on the adjusting dowel 41. Turn and tighten the nut 42 when the tension of the rope meets the request. For controlling the tension of the rope, a torque screwdriver may be applied for rotating the adjusting dowel 41. When the torque imposed on the screwdriver reaches the setting, the output torque of the screwdriver is invariant for skidding inside the screwdriver. In this case, the tension of the rope meets the request.

The tension of the rope may also be estimated by measuring the change of the spring's length. After taking off the screwdriver for adjusting the adjusting dowel 41, clockwise torque is imposed on the adjusting dowel 41 by the tensile force from the rope and the spring. The adjusting dowel 41 has a tendency to rotate clockwise under the action of this torque. The dowel cap 41d of the adjusting dowel 41 and the nut 42 have a tendency to move toward each other. Because the dowel cap 41d has a tendency to rotate relative to the journal stirrup 3f, a resistance moment signed T1 is imposed on the adjusting dowel 41 for resisting clockwise rotation of the adjusting dowel 41. Because the screws 41e of the adjusting dowel 41 have a tendency to rotate relative to the nut 42, another resistance moment signed T2 is imposed on the adjusting dowel 41. T1 keeps direct ratio with the axial pressure between the dowel cap 41d and the journal stirrup 3f, T2 keeps direct ratio with the axial pressure between the dowel screw part 41e and the nut 42. The two axial pressures are equal and determined by the tension of the nut 42. In other words, T1 and T2 are decided by the tension of the nut 42. Tightening the nut 42 with force as large as possible and then taking off the screwdriver for adjusting the adjusting dowel 41, if the adjusting dowel 41 may rotate clockwise, it should overcome the resistance moment produced by the nut 42.

In one embodiment, the clockwise rotation of the adjusting dowel 41 may be avoided by large enough resistance moment, and then the rope may keep tight. If there is little clockwise rotation of the adjusting dowel 41, the movement toward each other is formed between the dowel cap 41d and the nut 42. The pressure between the nut 42 and the journal stirrup 3g becomes larger, and the nut 42 becomes tighter than before. In other words, the connection between the adjusting dowel 41 and the nut 42 only can become tighter. In this case, the resistance moment for resisting the adjusting dowel 41 clockwise rotation becomes larger, and the adjusting dowel 41 is more difficult to rotate clockwise.

If the direction of tightening the screw joint by rotating the adjusting dowel 41 relative to the nut 42 is the same as the rotating tendency direction of the adjusting dowel 41 under the action of the pull of the rope, the whole mechanism for adjusting the length of the rope can achieve self-lock. Increasing the effective length of the first rope 17 may be accomplished by loosening the nut 42, then rotating the adjusting dowel 41 clockwise and releasing a certain part of the first rope 17 twisted on the adjusting dowel 41, and then tightening the nut 42.

Figure 8:
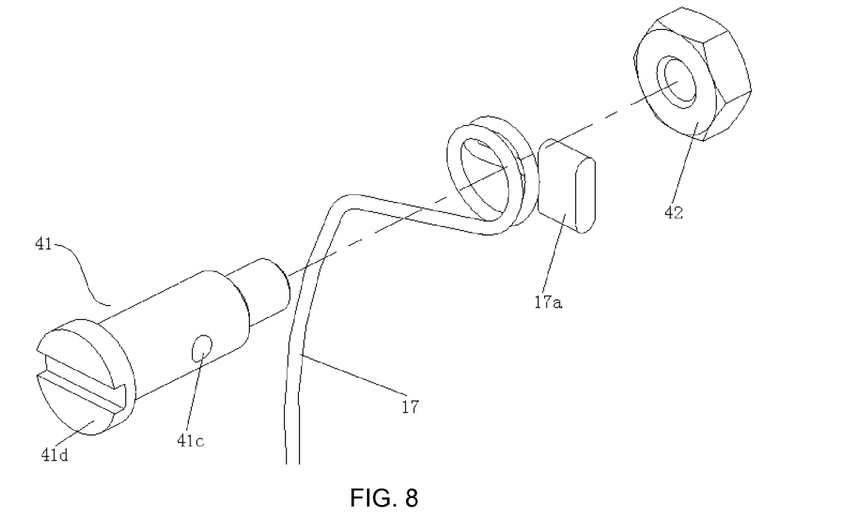
FIG. 8 is an exploded view of a method for connecting a rope and a dowel.

The difference between the aforementioned embodiments is the connecting method between the first rope 17 and the adjusting dowel 41 shown in FIG. 8. A through-hole 41c may be disposed in the adjusting dowel 41. Before assembling the first rope 17, the knot 17a may not be produced. When assembling the first rope 17, firstly, the adjusting dowel 41 is inserted into the hole 3a and 3b of the driven wheel 3. Secondly, the first rope 17 without the knot 17a passes through the through-hole 41c. Thereafter, the knot 17a may be produced on the end of the first rope 17. The knot 17a may be produced by riveting, that is, the end of the first rope 17 passes through a metal sleeve, and then the sleeve is flattened. For this connecting method, the knot 17a should be produced after the first rope 17 passes through the through-hole 41c of the adjusting dowel 41.

In one embodiment, the effective length of the rope driving the driven wheel is adjusted by rotating the adjusting dowel. The precision request of the ropes length is significantly reduced. When assembling the ropes, it is not needed to impose pull force directly on the spring, but to rotate the adjusting dowel instead. The function for adjusting the tension of the rope is achieved. Because of the resistance moment is formed by the axial pressure force between the dowel cap and the nut, it is difficult to rotate the dowel and loose the rope.

In one embodiment, rather than a nut, a screw thread hole on the driven wheel away from the dowel cap 41d may be used. A screw hole on the driven wheel 3 may also be used for cooperating with the adjusting dowel 41 directly, wherein the adjusting dowel 41 is inserted, and the ropes twist on the adjusting dowel 41. The length of the rope may be adjusted by rotating the adjusting dowel 41 clockwise and counter-clockwise.

In the transmission system, a gear may be used instead of the timing pulley transmission, even the transmission wheel may be canceled, connecting the driving shaft with the motor directly. Only one rope may be used in one embodiment, the middle of the rope connecting with the driving shaft and the two ends of the rope connecting with the driven wheel and the adjusting dowel respectively.

Two adjusting dowels may be used in one embodiment. These adjusting dowels are coupled to the driven wheel. If using only one rope, the two ends of the ropes should connect with the two adjusting dowels respectively. If two ropes is adopted, each rope connects with one rope adjusting dowel respectively.

The above-described embodiments are provided by way of example and not limitation. A skilled artisan can make several simple derivations or replacements without departing from scope of the invention. All such derivations or replacements shall fall within the scope of the invention.

What is claimed is:

1. A three-dimensional mechanical ultrasonic probe, comprising:
    a base;
    a transducer for emitting an ultrasonic signal;
    a driven wheel with a hole, the driven wheel being connected to the transducer, the transducer being swung by the driven wheel;
    a motor fixed on the base; and
    a transmission system connected to the motor and a first rope, the transmission system being driven by the motor, the first rope being driven by the transmission system;
    wherein the first rope is connected to the transmission system and a rope adjusting dowel and wherein at least a portion of the first rope is wound around the rope adjusting dowel;
    wherein the rope adjusting dowel is pivotably inserted into the hole of the driven wheel; and
    wherein the rope adjusting dowel includes a waist-shaped hole and a slot, a knot of the first rope passing through the waist-shape hole and being blocked by the slot.

2. A three-dimensional mechanical ultrasonic probe according to claim 1, wherein the driven wheel includes two concentric holes where the rope adjusting dowel inserted, and the adjusting dowel can rotate in the two concentric holes.

3. A three-dimensional mechanical ultrasonic probe according to claim 1, wherein the rope adjusting dowel includes a through-hole, the rope being connected to the adjusting dowel by passing through the through-hole.

4. A three-dimensional mechanical ultrasonic probe according to claim 1, further comprising a nut, the nut being coupled to the rope adjusting dowel, wherein the direction of tightening the screw joint by rotating the rope adjusting dowel relative to the nut is the same as the rotating tendency direction of the adjusting dowel under the action of the pull of the rope.

5. A three-dimensional ultrasonic probe according to claim 1, wherein the transmission system includes a driving timing pulley, a driven timing pulley and a driving shaft, the driving timing pulley connecting with the output of the motor and driving the driven timing pulley by a timing belt, wherein the driven timing pulley drives the driving shaft connected to the first rope.

6. A three-dimensional ultrasonic probe according to claim 1, further comprising a second rope, one end of the second rope connecting with the transmission system, wherein the driven wheel includes a second spring connecting with the other end of the second rope.

* * * * *